United States Patent
Ellis

(10) Patent No.: US 8,162,945 B2
(45) Date of Patent: Apr. 24, 2012

(54) DRILL BIT AND METHOD FOR PRODUCING A DRILL BIT

(75) Inventor: Liam Patrick Ellis, Fairlight (AU)

(73) Assignee: Surgibit IP Holdings Pty Limited, Fairlight, NSW (AU)

( * ) Notice: Subject to any disclaimer, the term of this patent is extended or adjusted under 35 U.S.C. 154(b) by 597 days.

(21) Appl. No.: 12/243,786

(22) Filed: Oct. 1, 2008

(65) Prior Publication Data

US 2009/0216235 A1     Aug. 27, 2009

Related U.S. Application Data

(63) Continuation of application No. 10/513,259, filed as application No. PCT/AU03/01003 on Aug. 7, 2003, now Pat. No. 7,892,235.

(30) Foreign Application Priority Data

Aug. 8, 2002 (AU) ................................ 2002950673
Nov. 8, 2002 (AU) ................................ 2002953610

(51) Int. Cl.
   *A61B 17/00* (2006.01)
(52) U.S. Cl. ........................................................ 606/80
(58) Field of Classification Search ................... 606/80; 408/199, 227–230
   See application file for complete search history.

(56) References Cited

U.S. PATENT DOCUMENTS

| | | | |
|---|---|---|---|
| 1,859,202 A | 5/1932 | Emmons | |
| 2,391,396 A * | 12/1945 | Denison | 408/230 |
| 2,404,048 A * | 7/1946 | Gepfert | 408/228 |
| 2,640,379 A * | 6/1953 | Graves | 408/228 |
| 3,626,645 A | 12/1971 | Rochet | |
| 4,116,580 A * | 9/1978 | Hall et al. | 408/230 |
| 4,222,690 A * | 9/1980 | Hosoi | 408/230 |
| 4,362,161 A * | 12/1982 | Reimels et al. | 606/173 |
| 5,007,911 A | 4/1991 | Baker | |
| 5,553,682 A | 9/1996 | Batliner et al. | |
| 5,664,914 A | 9/1997 | Taniguchi | |
| 6,312,432 B1 | 11/2001 | Leppelmeier | |

FOREIGN PATENT DOCUMENTS

GB     608747     9/1948

(Continued)

OTHER PUBLICATIONS

Supplementary European Search Report for European Patent Application Serial No. 03783839.8-1265, mailed Jun. 2, 2009.
Canadian Intellectual Property Office, Official action in Canadian Application No. 2,494,062, dated Apr. 6, 2010.

(Continued)

*Primary Examiner* — Nicholas Woodall
(74) *Attorney, Agent, or Firm* — McAndrews, Held & Malloy, Ltd.

(57) ABSTRACT

A drill bit including a shaft which has a pyramidal shaped end defining a drill tip with a plurality of edges defining the pyramidal shape.
One or more recesses are provided for directing away debris produced while drilling, the at least one recess having a first portion extending along the shaft and a second portion having a first portion extending along the shaft and a second portion which extends along the drill tip; wherein the. The second portion which extends along the drill tip. The second portion of the at least one recess extends along an edge of the drill tip.

19 Claims, 11 Drawing Sheets

FOREIGN PATENT DOCUMENTS

| | | |
|---|---|---|
| GB | 2 181 076 | 4/1987 |
| JP | 02-292106 | 12/1990 |
| JP | 07-329049 | 12/1995 |
| JP | 08-019911 | 1/1996 |
| JP | 2607658 | 5/1997 |
| JP | 11-510103 | 9/1999 |
| WO | WO 97/04908 | 2/1997 |

OTHER PUBLICATIONS

Japanese Patent Office, Official action in Japanese Application No. 2004-526505, dated Apr. 9, 2010.

Office Action from the Japanese Patent Office mailed Aug. 25, 2009.

* cited by examiner

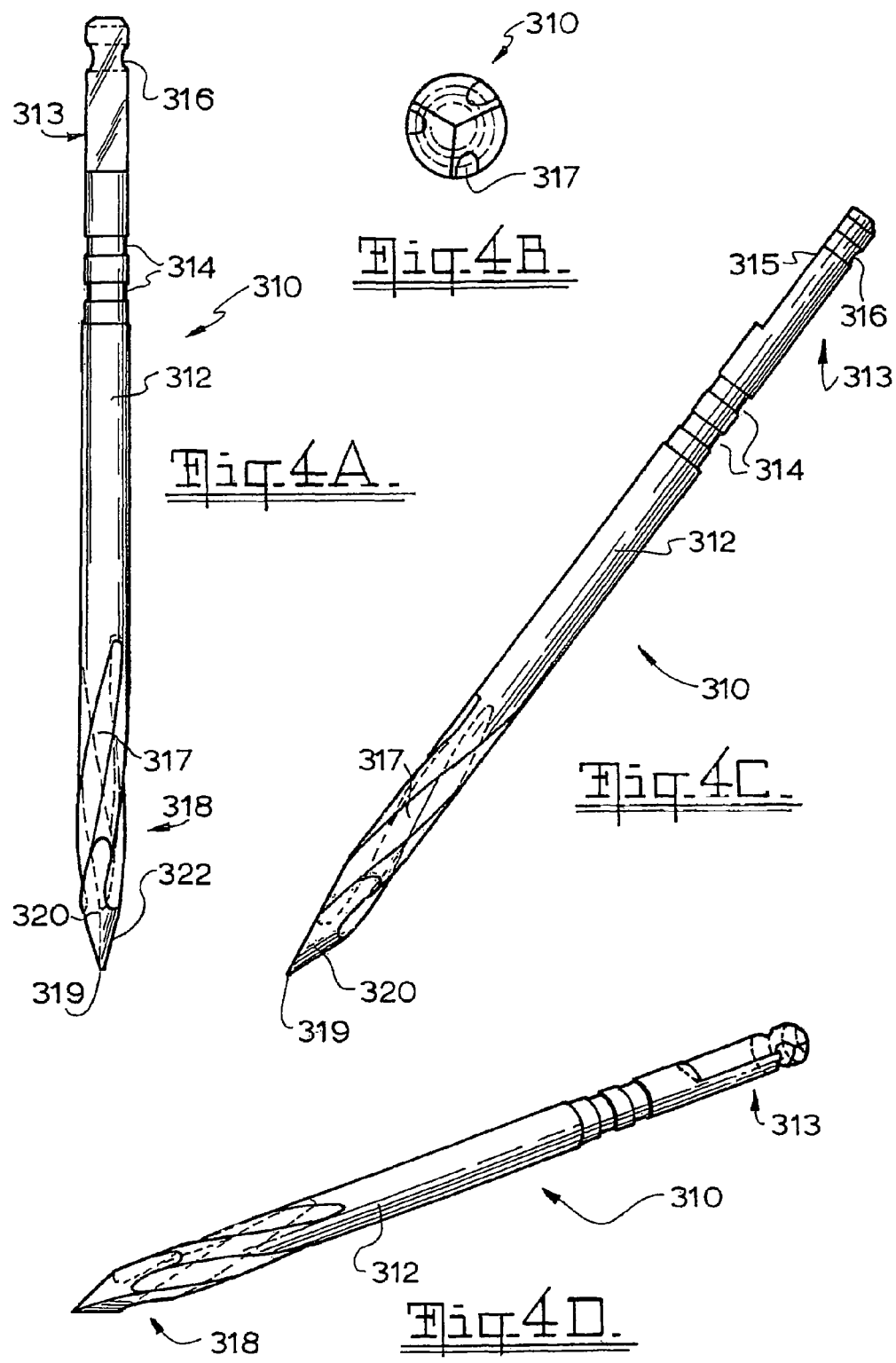

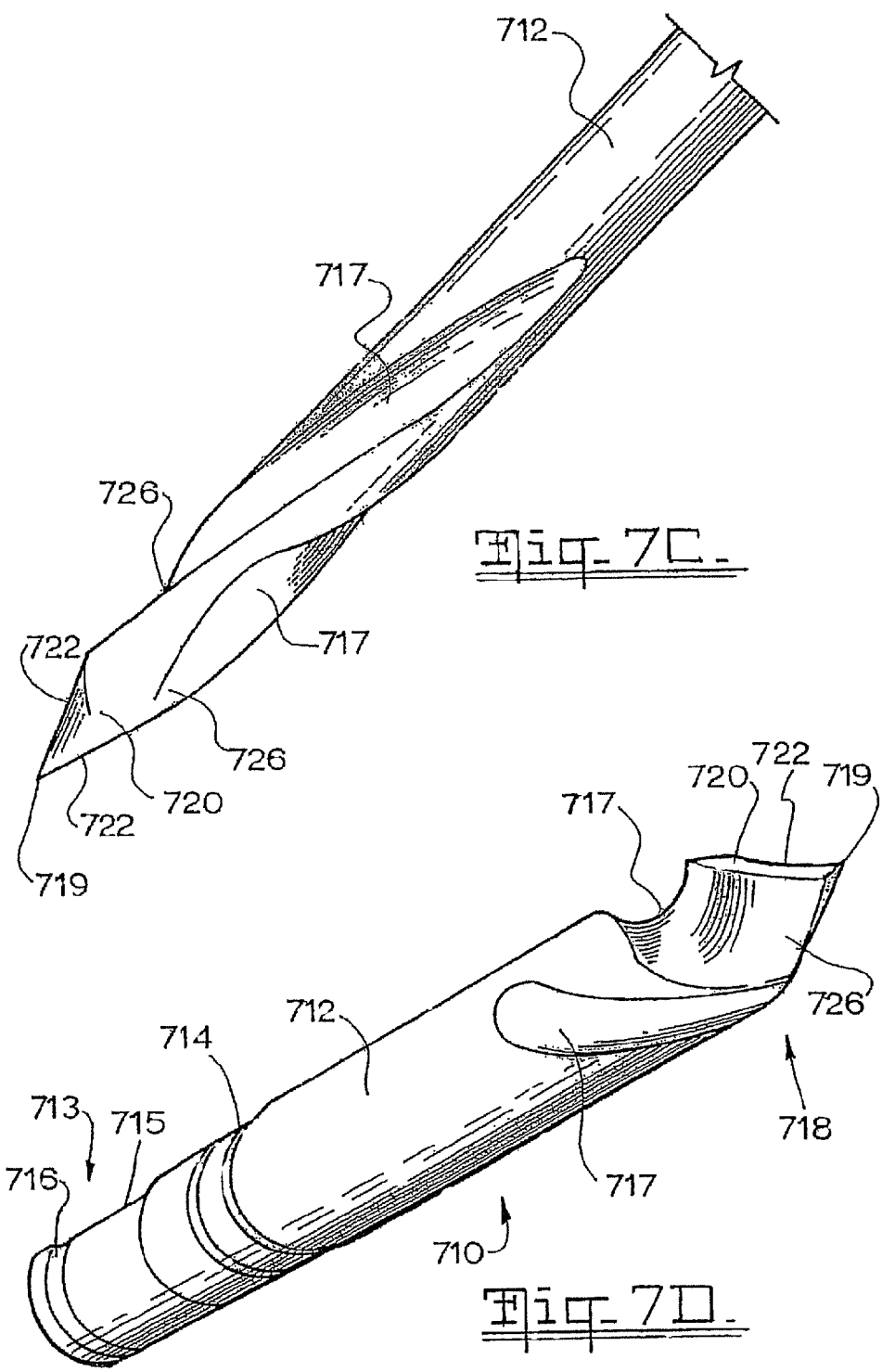

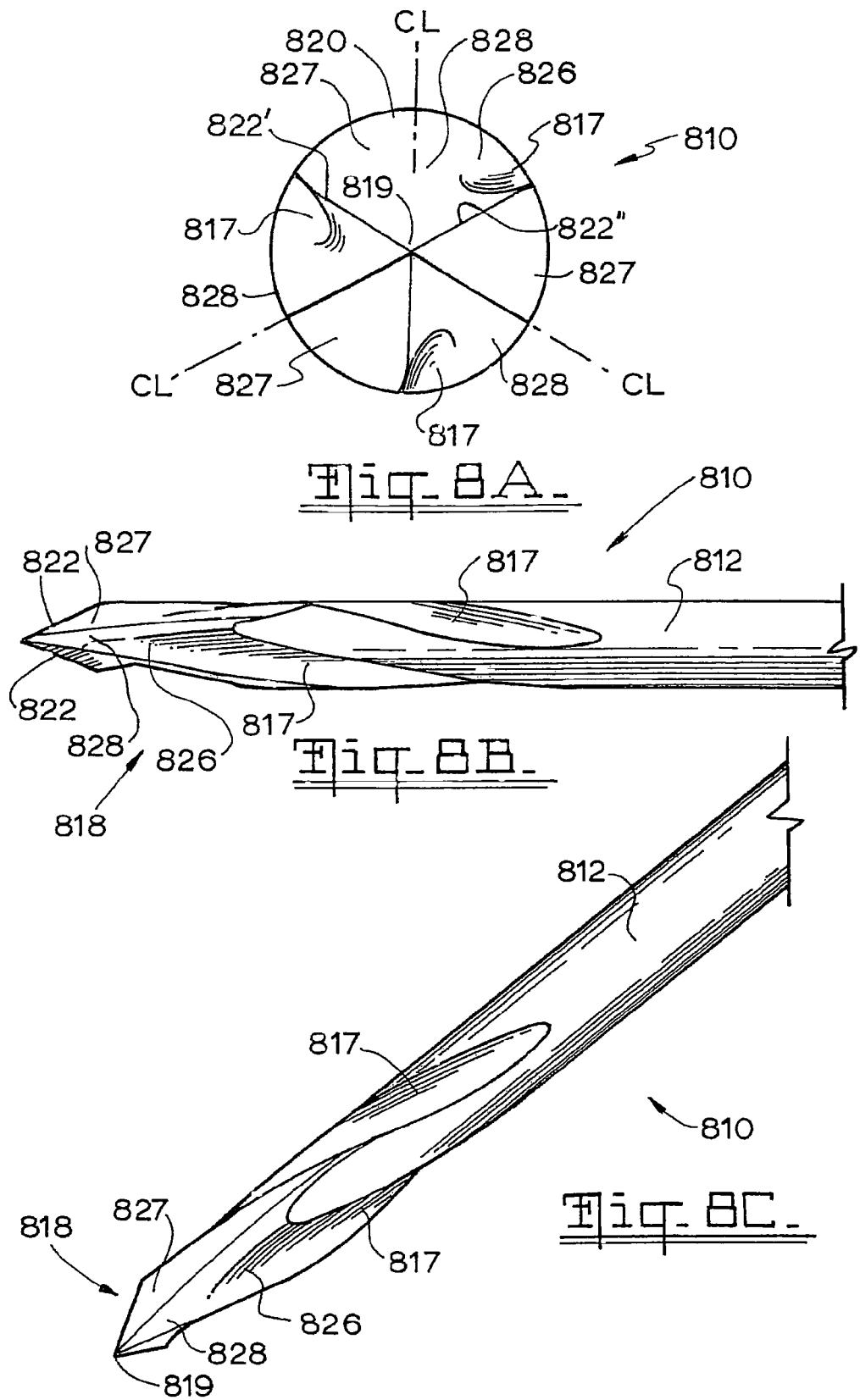

DRILL BIT AND METHOD FOR PRODUCING A DRILL BIT

RELATED APPLICATIONS

This is a continuation of U.S. patent application Ser. No. 10/513,259 which is the national stage (filed on May 11, 2005) of International Application Serial No. PCT/AU2003/001003, having an international filing date of Aug. 7, 2003, which claims priority to Australian Patent Application Serial No. 2002950673, filed Aug. 8, 2002 and Australian Patent Application Serial No. 2002953610, filed Nov. 8, 2002.

FIELD OF THE INVENTION

The present invention relates to a drill bit and method for producing a drill bit, and is of particular but by no means exclusive application to drilling bones, cartilage and similar structures during orthopaedic surgery.

SUMMARY OF THE INVENTION

According to a first aspect of the present invention, there is provided a drill bit comprising:

a shaft which has a pyramidal shaped end defining a drill tip with a plurality of edges defining the pyramidal shape; and one or more recesses for directing away debris produced whilst drilling, the or each recess having a first portion extending along the shaft and a second portion which extends along the drill tip, wherein the second portion of the or each recess extends along an edge of the drill tip.

Preferably, each edge defines a cutting edge and preferably the or each recess, is located to further define the cutting edge.

Preferably each edge extends from the shaft to a remote point of the drill tip.

By employing a cutting edge the drill tip can quickly create a securing hole which secures the drill bit in position so as to prevent the drill bit from moving over the surface of the material when starting to drill.

Preferably, the depth of the second portion of each of the recesses varies along a length thereof relative to a surface of the drill tip so that the cutting ability of the edge adjacent to the point of the drill bit is less than the cutting ability of the edge adjacent to the shaft.

By reducing the cutting ability of the cutting edge adjacent to the point, the drill bit is less likely to break when drilling is commenced. This is because the edge adjacent to the point is less likely to lock with the material into which the drill is entering.

Preferably, the first portion of the or each recess is substantially helical in shape, whilst the second portion of the or each recess is substantially straight.

Preferably, the drill tip includes at least three edges which define the pyramidal shape of the drill tip.

Preferably, at least three corresponding surfaces extend between the three edges. Prior to forming the or each recess the surfaces may be flat (planar) or concave with respect to the drill bit.

Preferably, the second portion of the or each recess extends along a respective one of the surfaces.

Preferably, the edge of the drill tip is bevelled so as to enhance the cutting ability of the cutting edge.

According to a second aspect of the present invention, there is provided a method for producing a drill bit, including the steps of:

forming a shaft which has a pyramidal shaped end defining a drill tip with a plurality of edges defining the pyramidal shape; and forming one or more recesses for directing away debris produced whilst drilling, the or each recess having a first portion extending along the shaft and a second portion which extends into the drill tip, wherein the second portion of the or each recess extends along an edge of the drill tip.

Preferably, the step of forming the one or more recesses includes moving a grinding element outwardly from the drill tip as it moves therealong such that the depth of the second portion of each of the recesses varies along a length thereof relative to a surface of the drill tip.

Preferably, the or each recess is formed adjacent to a respective edge such that the cutting ability of the edge adjacent to a point of the drill tip is less than the cutting ability of the edge adjacent to the shaft.

According to a third aspect of the present invention, there is provided a drill bit comprising:

a shaft having a drilling end defining a drill point;

at least one face that extends to and helps define the drill point, the or each face generally subtending an acute angle with a longitudinal axis of the shaft; and at least one flute defined in the shaft for directing away debris produced during drilling, with the at least one flute intersecting with the at least one face, such that, in end view, the flute is offset from a central part of the face.

By offsetting the flute in this manner, the present inventor has discovered that eg. bone debris can be rapidly released and directed away from the drill end, and yet a strong drill point can be formed which can be securely located at the bone. The inventor has observed that a strong point can be forced through the periosteum to provide a means against slippage and to then enable rapid drilling of the bone. Such a drill point may also preliminarily puncture the bone and then, when driven, cut away the bone, the flute location then rapidly directing away debris produced during such cutting.

Preferably, the flute intersects the face in a manner that defines a continuous curve at the flute-face intersection.

This curving further enhances and smoothes the directing away of debris produced during bone drilling.

Preferably the or each face:

(a) is flat, being defined as a bevel;
(b) is curved or v-shaped concavely into the shaft;
(c) has a chamfer or a v-shaped groove along one edge thereof.

Thus, in the third aspect when it is stated that the face generally subtends an acute angle with a longitudinal axis of the shaft, for curved faces this acute angle is represented by an imaginary line drawn from the drill point to where the face meets the shaft exterior surface.

In (a) the provision of one or more flat bevelled faces at the drilling end enables a rapid and precise formation of the drill point, and also provides a definite and strong point structure to maximise the life of the drill point. In (b) and (c) the concave shaping of the face can enhance its capacity to cut and may even further strengthen the drill point.

Preferably, in (c) the flute extends into the face adjacent to said one edge.

Optionally in (c) the flute can intersect with the v-shaped groove.

This further enhances the directing away of debris produced during drill cutting.

In one preferred form three faces are provided at the drilling end, each evenly offset with respect to the other two and each tapering down to the drill point to provide the drill end with the appearance of a triangular pyramid. Preferably in this regard a respective flute is provided to intersect with each face.

In an alternative form four faces can be provided at the drilling and, each evenly offset with respect to adjacent faces on either side thereof and each tapering down to the drill point to provide the drill end with the appearance of a square pyramid. In this regard a respective flute can be provided just to intersect with each of only two of the faces, being opposing faces at the drill end (or a flute for each face may also be provided).

Whilst three or four faces have been found to be optimum, any number of faces at the drilling end may be employed as appropriate.

Preferably, the or each flute extends generally spirally away from its respective face and at least part way along the shaft.

Typically the fluting does not extend for the full length of the shaft to provide, for example, an unfluted part of the shaft which can be inserted into the drive of a drill.

According to a fourth aspect of the present invention, there is provided a drill bit comprising:

shaft having a drilling end defining a drill point;

at least one face that extends to and helps define the drill point, the or each face generally subtending an acute angle with a longitudinal axis of the shaft; and at least one flute defined in the shaft for directing away debris produced during drilling, with the at least one flute intersecting with the at least one face such that a continuous curve is defined at the flute-face intersection.

According to a fifth aspect of the present invention, there is provided a drill bit comprising:

a shaft having a drilling end defining a drill point;

at least one face that extends to and helps define the drill point, the or each face generally subtending an acute angle with a longitudinal axis of the shaft; and at least one flute defined in the shaft for directing away debris produced during drilling, with the at least one flute intersecting with the at least one face, wherein the or each face:

(a) is curved or v-shaped concavely into the shaft;

(b) has a chamfer or a v-shaped groove along one edge thereof.

Preferably, the surgical drill bit of the second and third aspects is otherwise as defined in the third aspect.

BRIEF DESCRIPTION OF SEVERAL VIEWS OF THE DRAWINGS

Notwithstanding any other embodiments which may fall within the scope of the present invention, a preferred embodiment of the present invention will now be described, by way of example only, with reference to the accompanying drawings, in which:

FIGS. 4A to 4D respectively show front, end, side and perspective views of the second drill bit of FIG. 3, but in outline;

FIGS. 7A to 7D respectively show an enlarged end, and side, perspective and reverse perspective views of a fifth drill bit in accordance with the preferred embodiment of the present invention;

FIGS. 8A to 8C respectively show an enlarged end, and side and perspective views of a sixth drill bit in accordance with the preferred embodiment of the present invention;

PREFERRED EMBODIMENT OF THE PRESENT INVENTION

Figure 1:
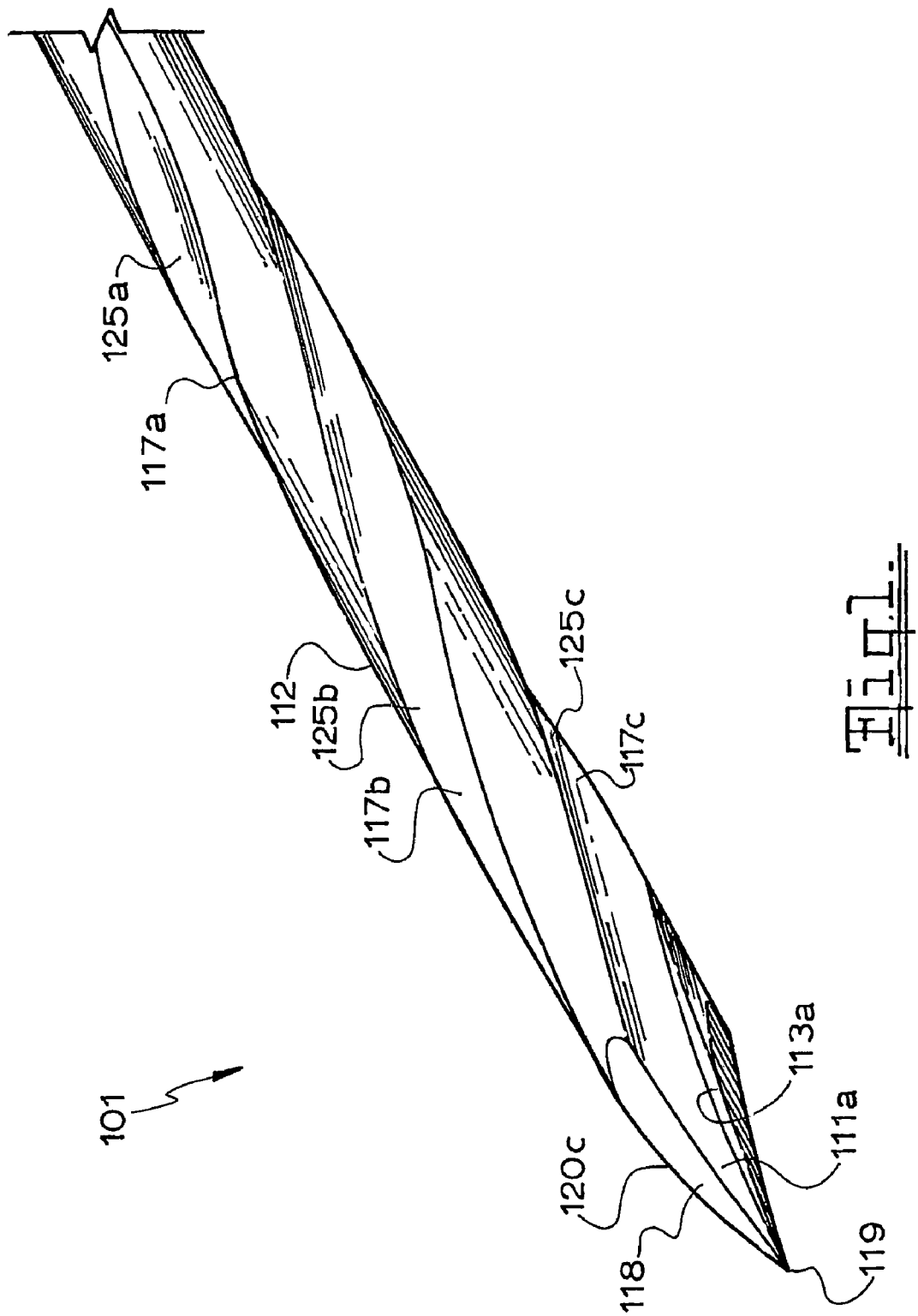
FIG. 1 illustrates a perspective view of a first drill bit according to a preferred embodiment of the present invention.
Figure 2:
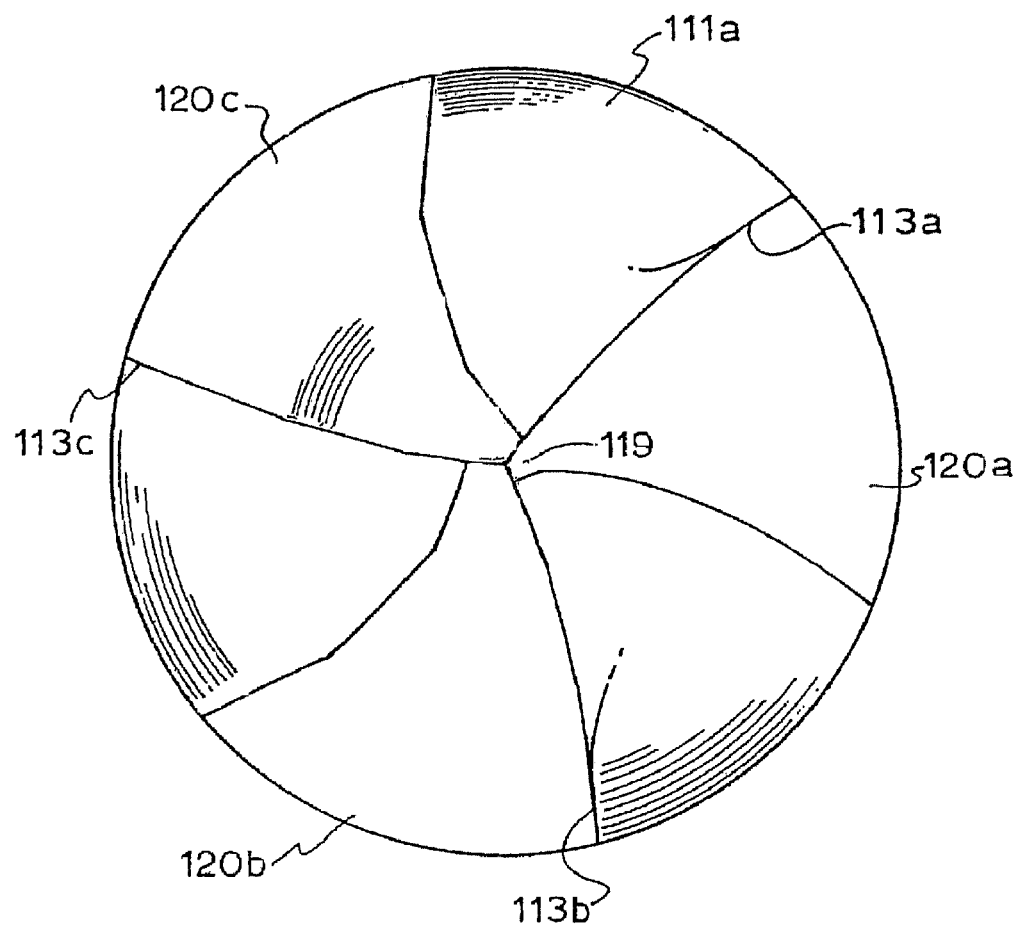
FIG. 2 illustrates an end view of the first drill bit shown in FIG. 1.

FIGS. 1 and 2 show a first drill bit 101 according to the preferred embodiment of the present invention. The drill bit 101 includes a shaft 112 which has a pyramidal shaped end 118 defining a drill tip. The material from which the drill bit 101 is made depends on the intended application of the drill bit 101. However, for orthopaedic surgery, the drill bit 101 is made from surgical quality stainless steel. Whilst not illustrated in FIG. 1, the other end of the drill bit 101 is adapted for mounting in a motorized drill chuck. For example, the other end of the drill bit 101 can be provided with a series of graduations, a cut-away and a circumferential groove in the shaft 112 adjacent the other end so as to facilitate its coupling in the chuck of a drive of a motorised surgical drill. The graduations can be used to indicate depth of insertion of the drill bit into the drive chuck and into the patient.

The drill bit 101 also includes three recesses in the form of grooves 117a, 117b and 117c (collectively referred to as reference numeral 117), each of which includes a first portion 125a, 125b and 125c (collectively referred to as reference numeral 125) extending at least partway along the shaft 112 and a second portion 111 a, 111 b and 111 c (collectively referred to as reference numeral 111) which extends edges 113a, 113b and 113c (collectively referred to as reference numeral 113) of the drill tip. Typically edges 113 define a cutting edge. The edges 113 also include bevelling so as to enhance the cutting ability of the cutting edge. The grooves 117 allow debris which is produced whilst drilling to be channeled away from the hole while being drilled. The first portion 125 of each of the grooves 117 spirals along the shaft 112 so as to form of a helix, whilst the second portion 111 is substantially straight (that is, tending to align with a longitudinal axis of the shaft). Each of the grooves 117 typically has an arcuate semi-cylindrical shape in cross-section and along its length. However, other suitable profiles such a V-shape or square shape may be employed.

The depth of the second portion 111 of each of the grooves 117 varies along the length of the second portion 111 relative to the surface of the drill tip in which the second portion 111 is located. More specifically, the depth of the second portion 111 of each of the grooves 117 becomes shallower towards the point 119 of the drill bit 101. This provides the portion of the cutting edge 113 located nearer the point 119 with a lesser cutting ability than the portion of the cutting edge 113 located nearer the shaft 112. The advantage of this is that the drill tip is less likely to break as a result of locking with the material into which the drill bit 101 is entering.

The pyramidal shaped end 118 is formed from three elongate surfaces 120a, 120b and 120c (collectively referred to as reference numeral 120), but more surfaces can be employed if desired. Increasing the number of surfaces to define the pyramidal shaped end 118 results in more edges 113 which can define more cutting edges.

Also, the pyramidal shaped end 118 is relatively longer than the drill tip of existing drills. This provides an extreme point 119 which assists in securely locating the drill bit 101 so as to prevent movement thereof when drilling is started. The assistance is provided as a result of the extreme point 119 piercing the periosteum and puncturing the outer surface of the bone, thereby locating the drill bit 101 in place prior to drilling. Each of the surfaces forming the pyramidal shaped end 118 subtends an angle with the longitudinal axis of the drill bit 101. The angle is typically around 30°, but may be varied depending on the application (for example, hardness of the material to be drilled).

As mentioned previously, the drill bit 101 is made from a material that is suitable for the intended application. For example, where the drill bit 101 is intended to be used in orthopaedic surgery the drill bit 101 is made from surgical quality stainless steel. The drill bit 101 is made from a blank rod of the appropriate material. Using a suitable grinder, one of the ends of the blank rod can be ground down so as to form the pyramidal shaped end 118 and adapt the other end of the drill bit 101 so that the drill bit 101 can be retained by a chuck of a drill.

The grinding machine can also be used to form the grooves 117. When forming the first portion 125 of each of the grooves 117, the grinding wheel of the machine remains fixed so that the first portion 125 has a constant depth. However, when forming the second portion 111 of the grooves 117, the grinding wheel is gradually moved outwardly from the drill tip as it moves towards the point 119. Moving the grinding wheel outwardly results in the second portion 111 having a depth that varies along the length of the drill tip. This characteristic produces a cutting edge which has a lesser cutting ability about the point 119 and which increases in cutting ability towards the shaft 112. Having a lesser cutting ability at the point 119 reduces the likelihood of the point 119 breaking off when drilling is commenced due to the cutting edge locking with the material into which the hole is being drilled.

Figure 3A:
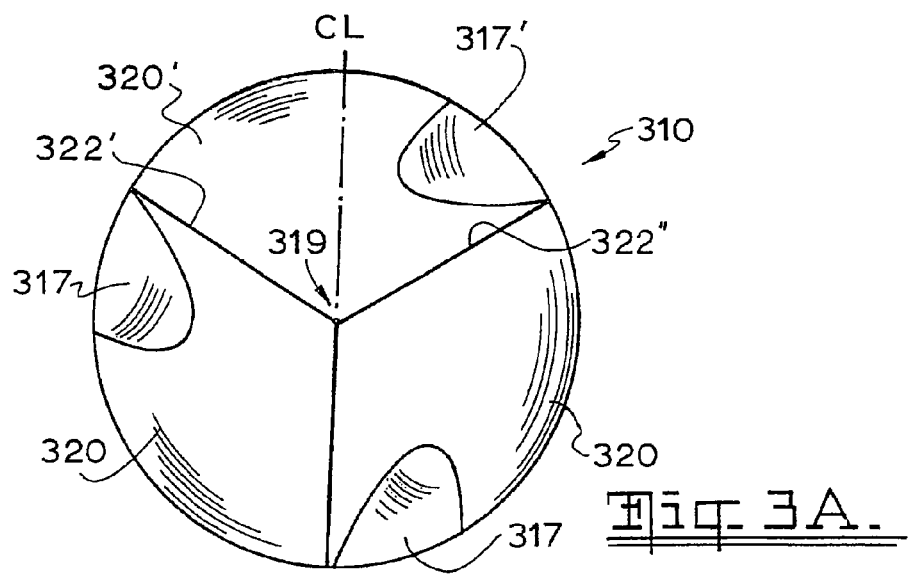
FIGS. 3A to 3C respectively show an enlarged end, and side and perspective views of a second drill bit in accordance with the preferred embodiment of the present invention.
Figure 3B:
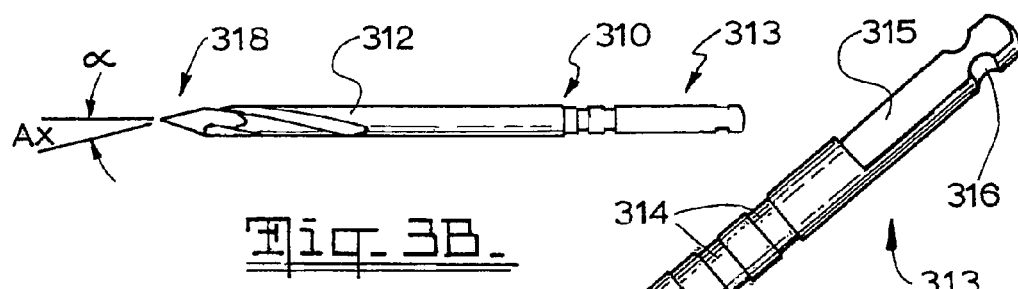
Figure 3C:
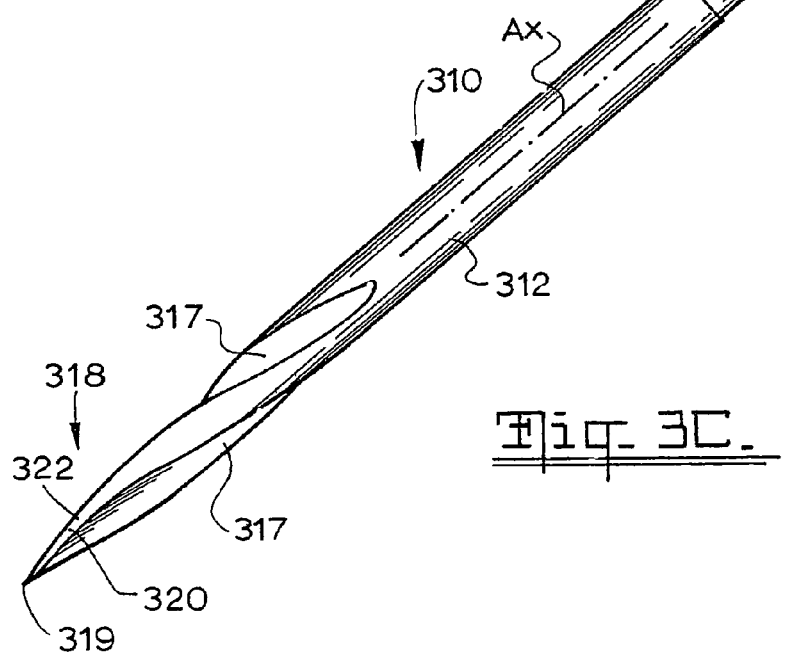

Referring to FIG. 3, which shows a second drill bit 310, the drill bit 310 includes a drill shaft 312, the opposite end 313 of which is adapted for mounting in a motorised drill chuck. For example, for orthopaedic procedures, the opposite end of the shaft can be provided with a series of gradations 314, a cut-away 315 and a circumferential groove 316 adjacent to end 313 to facilitate its coupling in the chuck of a drive of a motorised surgical drill. The gradations can be used to indicate depth of insertion of the drill bit in both the drive chuck and into a patient.

Three spiral flutes 317 extend from near the drilling end 318 and part way along the shaft 312. Each flute is typically an arcuate semi-cylindrical groove extending in the shaft, but may be V-shaped, square shaped etc. in cross-section. Each flute provides a passageway for the release of debris cut by the drill bit as it is inserted through a substrate (typically a bone). Usually two or three such spiral flutes are provided in the drill bit to maximise debris release.

A drill point 319 is provided at drilling end 318, the drill point being substantially elongated, tapered and pointed when compared with a conventional drill bit. In effect, the drill point is provided as a trocar-type formation.

Further, one or more, and typically three, bevelled faces 320 are provided and combine to define the drill point 319 at drilling end 318, each face subtending an angle α with a longitudinal axis AX through the shaft 312. Typically, the subtended angle α is around 30°, although it may be varied depending on the application (eg. hardness of material to be drilled). The three faces generally provide end 318 with a triangular pyramidal appearance.

Advantageously, the formation of bevelled faces 320 define cutting edges 322 along the side of each bevelled face which facilitate cutting and thus drilling into a bone or similar when the drill bit is rotated.

The formation of an extreme drill point 319 at drilling end 318 also enables the drill to be securingly located at a bone, piercing the periosteum and puncturing the outer surface of the bone to locate the drill bit in place prior to drilling.

In accordance with the present invention, and as best shown in FIG. 3A, each flute 317 intersects with a respective face 320 at a location that is offset from a centre line CL through the face 320. The advantage of this offsetting is that it facilitates maximum debris removal during cutting of bone, cartilage and other bodily material.

For example, referring to FIG. 3A, and assuming a counter clock-wise rotation of the drill, uppermost face 320' defines a leading edge 322' and a trailing edge 322". It will be see that flute 317' is located adjacent to the trailing edge. Thus, as the drill rotates and leading edge 322' cuts through a material, debris passes across and is accommodated by a maximal face area 320', prior to passing into flute 317'. This maximal face area prevents bunching or blocking of debris at the face and enhances debris release away from the drill point. Therefore, an optimal location for the intersection of each flute with its respective face is adjacent to the trailing edge for that face, as shown in FIG. 3A. Advantageously, rapid debris removal also facilitates more rapid drilling.

Figure 5A:
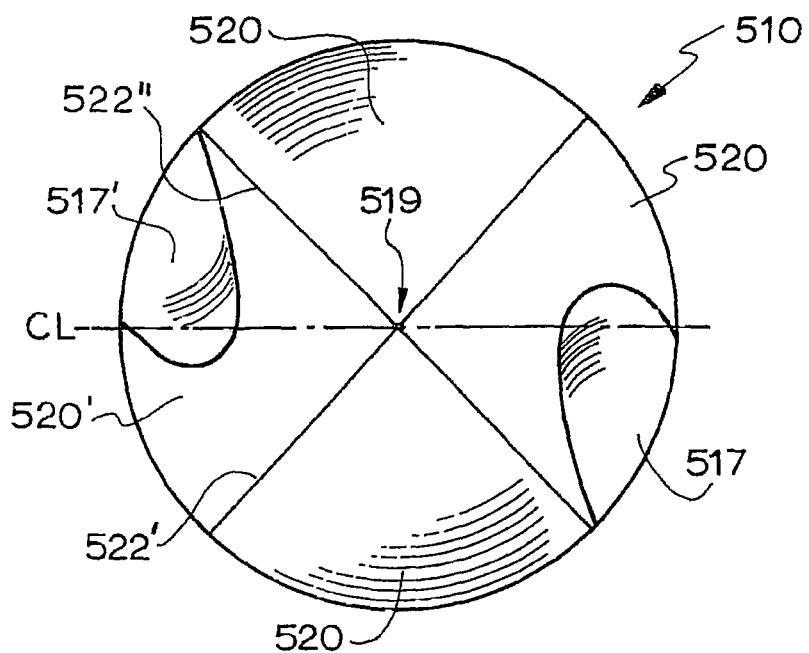
FIGS. 5A to 5C respectively show an enlarged end, and side and perspective views of a third drill bit in accordance with the preferred embodiment of the present invention.
Figure 5B:
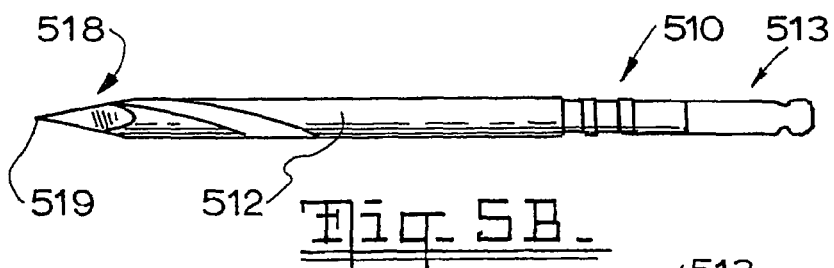
Figure 5C:
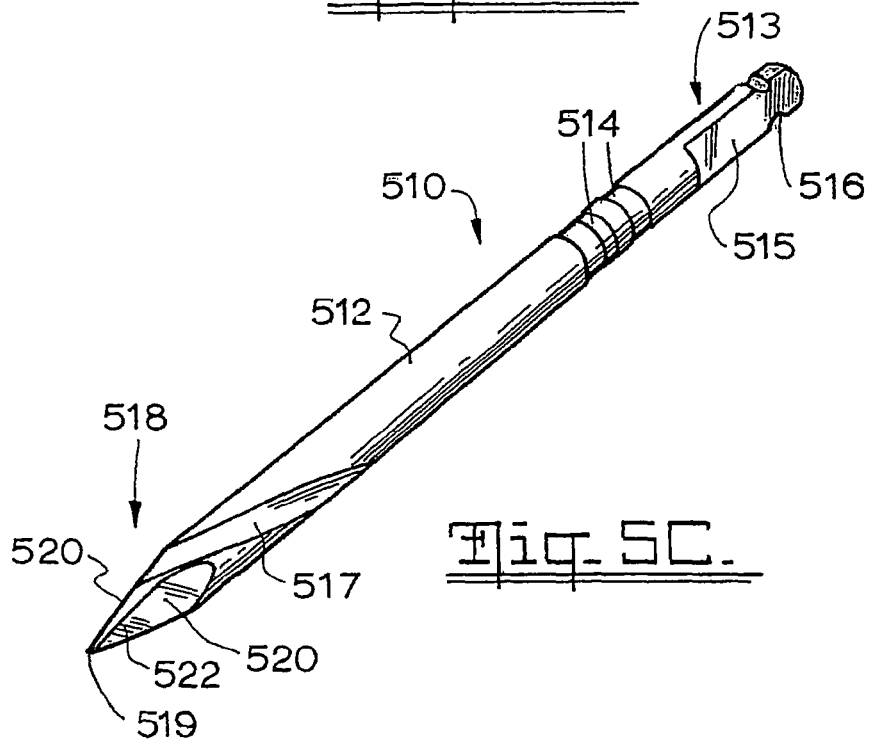

Referring now to FIGS. 5A to 5C, where like reference numerals are used to denote similar or like parts, drilling end 518 is now provided with four bevelled faces 520 (which in this embodiment are typically flat faces). The four faces generally provide end 518 with a square pyramidal appearance.

As can be clearly seen from FIG. 5A, only two of the faces (in this case two opposing faces) are provided with a flute 517 intersecting therewith. Again, these flutes are offset from a central part of their respective face to enhance debris removal as described above. The unfluted faces also provide an enhanced trocar-like affect to the drilling end 518.

It will also be seen in FIG. 5 that the flutes 517 are enlarged compared with the flutes of the drill bit of FIGS. 3 and 4. This is to ensure that the rate of debris release is maintained with the lesser flute number, and this also enables the flutes to pick up debris that passes across the unfluted faces (ie. as the drill rotates at rapid speeds). Otherwise, the operation of the drill bit is the same as the drill bit of FIGS. 3 and 4.

Figure 6A:
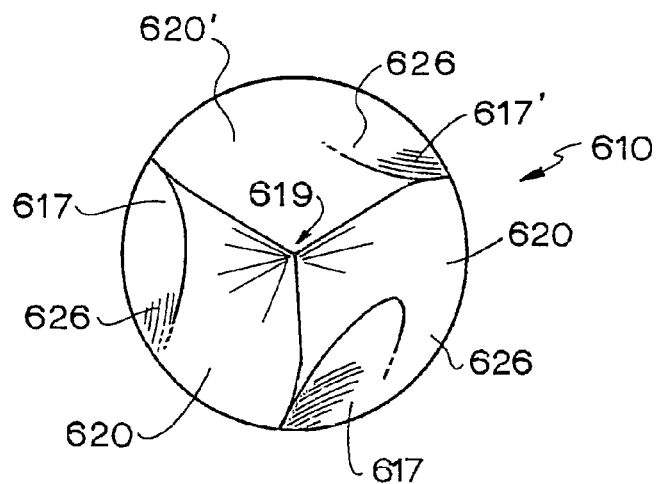
FIGS. 6A to 6C respectively show an enlarged end, and side and perspective views of a fourth drill bit in accordance with the preferred embodiment of the present invention.
Figure 6B:
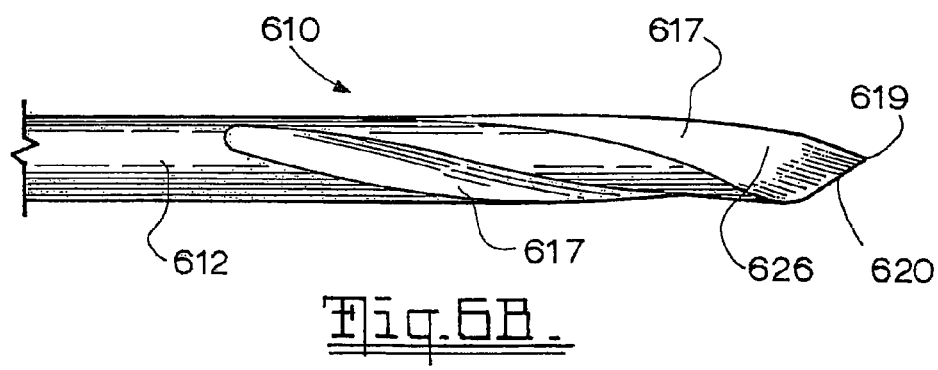
Figure 6C:
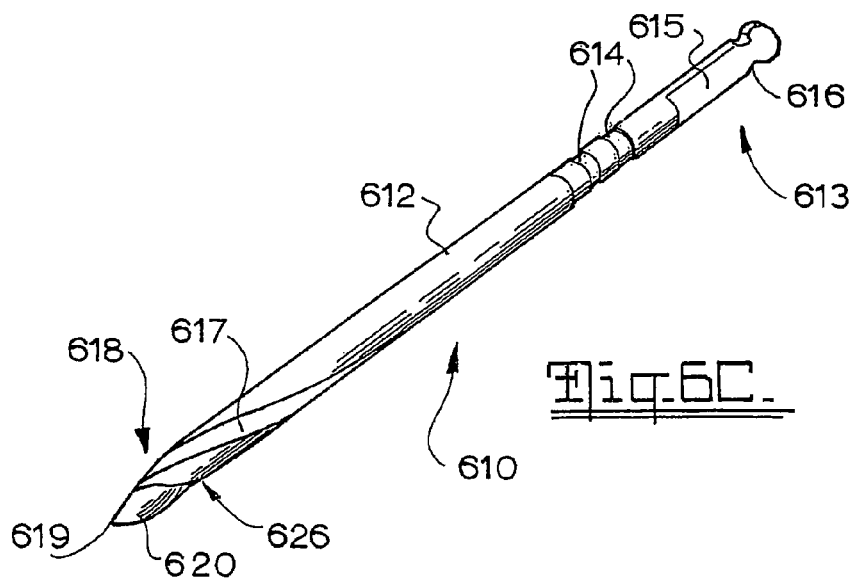

Referring now to FIG. 6, where like reference numerals are used to denote similar or like parts, a surgical drill bit having three faces at drilling end 618, similar to the drill bit of FIGS. 3 and 4, is shown. Each face also has a respective flute intersecting therewith, however, in this embodiment the intersection between the flute and its respective face is not abrupt but is gradual as facilitated by a continuous curved region 626. This region provides a kind of scalloping or concavity in each face 620, thus enhancing the definition of the drill point 619, but also providing a more pronounced channelling affect into each flute to guide and enhance the removal of debris cut by the rotating drill bit.

The more pronounced drill point facilitates easier drill bit location at slippery cutting surfaces and easier penetration. The region 626 facilitates more rapid removal of debris and thus even faster drill cutting.

Referring now to FIGS. 7A to 7D, the drill bit of FIG. 6 is further modified in that each face 720 is concaved inwardly with respect to the drill bit, defining an arcuate 3D scalloped surface. This is best seen with reference to FIG. 7D.

The effect of this scalloping is that the drill point 719 is even further pointed or sharpened, and the cutting edges become curved along their length and again are further sharpened (ie. because of the more rapid dropping away of each face 720 on either side of the cutting edge).

The drill bit of FIG. 7 also employs the continuous curved region 726 at the intersection of flute 717 and face 720 so that debris cut by the drilling end is rapidly conveyed away therefrom in use.

Figure 7A:
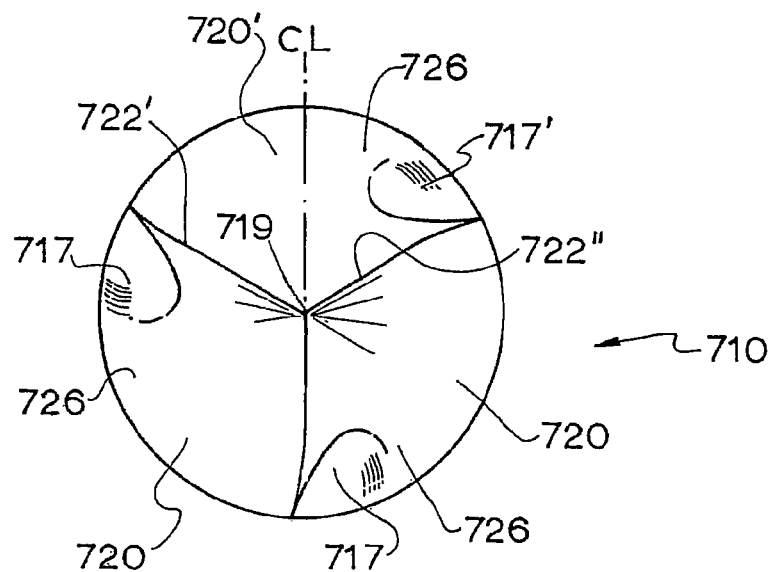
Figure 7B:
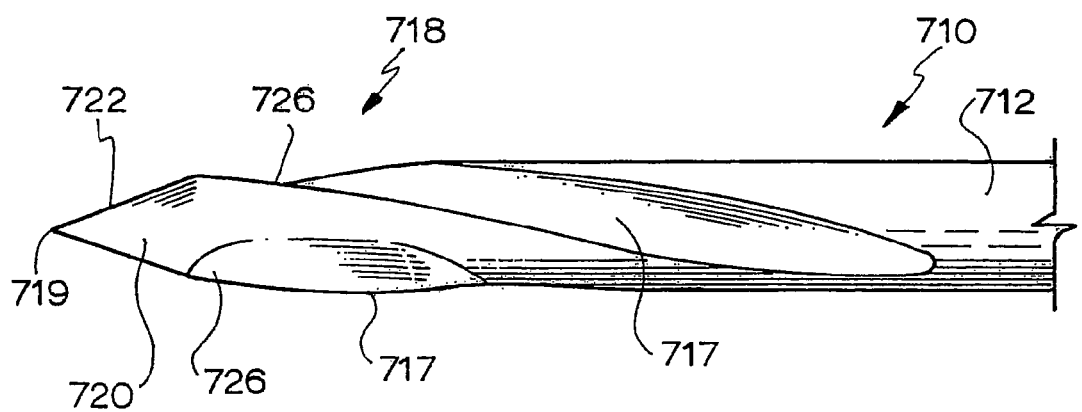

In FIG. 7, in end view (ie. FIG. 7A) the concave face is typically symmetrical about face centre line CL. However, the concave face can be defined asymmetrically about the centre line, for example, so that adjacent to the leading edge 722', the face slopes more steeply away, and slopes more gradually up towards the trailing edge 722". This asymmetric offset of the concavity at each face can sharpen the leading edge relative to the trailing edge and can enhance debris being directed towards flute 717 (ie. by pressure differentials etc.). The operation of the drill bit of FIG. 7 is in other respects similar to that previously described.

Referring now to FIG. 8, the inwardly concave curved face of FIG. 7 is replaced by two flat sub-faces 827 and 828. The sub-faces 827 and 828 in end view (ie. FIG. 8A) define face 820 as a type of tapering V-shaped groove (ie. tapering down to drill point 819). Again, the employment of a concave V-shaped face 820 sharpens or pronounces the edges 822, and also assists in directing debris towards flute 817 via curved region 826.

Again, typically the sub-faces 827 and 828 are arranged symmetrically about face centre line CL, but may be asymmetrically offset to eg. more steeply slope away from the leading edge 822' as opposed to the trailing edge 822". Again, this can define a sharper cutting edge and assist with the distribution of debris away from the drilling end● 818.

Figure 9A:
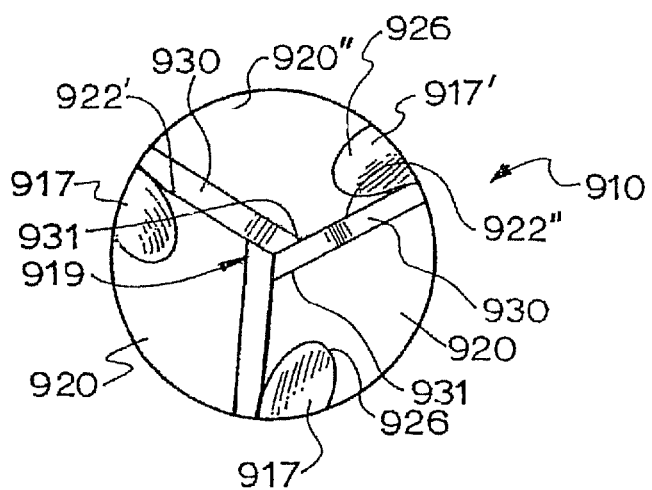
FIGS. 9A to 9C respectively show an enlarged end, and side and perspective views of a seventh drill bit in accordance with the preferred embodiment of the present invention.
Figure 9B:
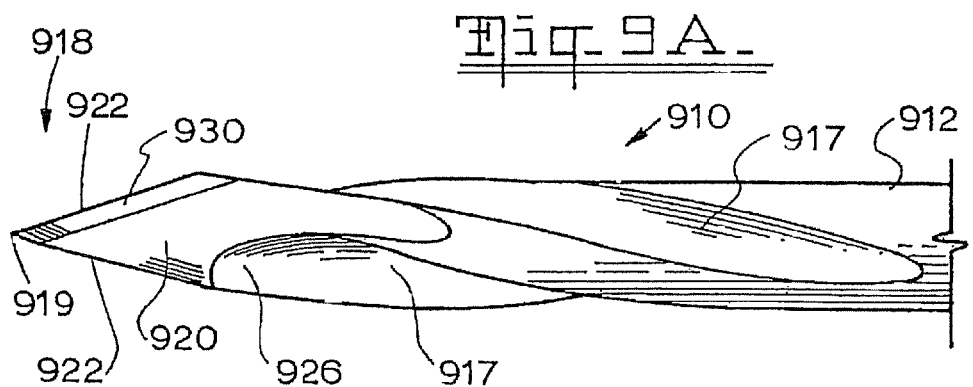
Figure 9C:
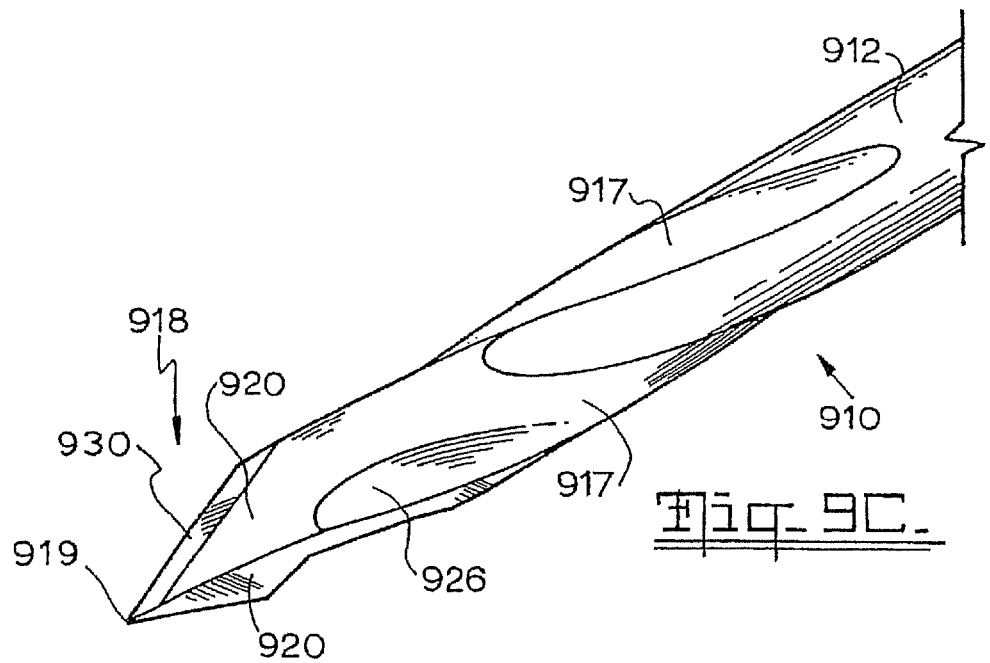

Referring now to FIGS. 9A to 9C, where like reference numerals are used to denote similar or like parts, a drill bit having either flat faces 920 as shown in FIG. 6, or curved faces as shown in FIG. 7 is depicted. In any case, in this embodiment a chamfer 930 is provided that slopes away from the leading edge 922 and into its respective face as best shown in FIG. 9A. As also best shown in FIG. 9A, a small section 931 of chamfer 930 continues on and extends partway up trailing edge 922", so that drill point 919 is defined by the merging of three chamfered faces and thus is unitary and pyramidal in shape (ie. trocar-like).

This chamfering arrangement increases the strength of the drill point and prevents it from breaking away where other point configurations might otherwise fail in extreme situations. Otherwise, the drill bit of FIG. 9 is similar in construction to the drill bit of FIGS. 6 and 7 and operates in a similar manner to the drill bits previously described.

Figures 10A, 10B, 10C:
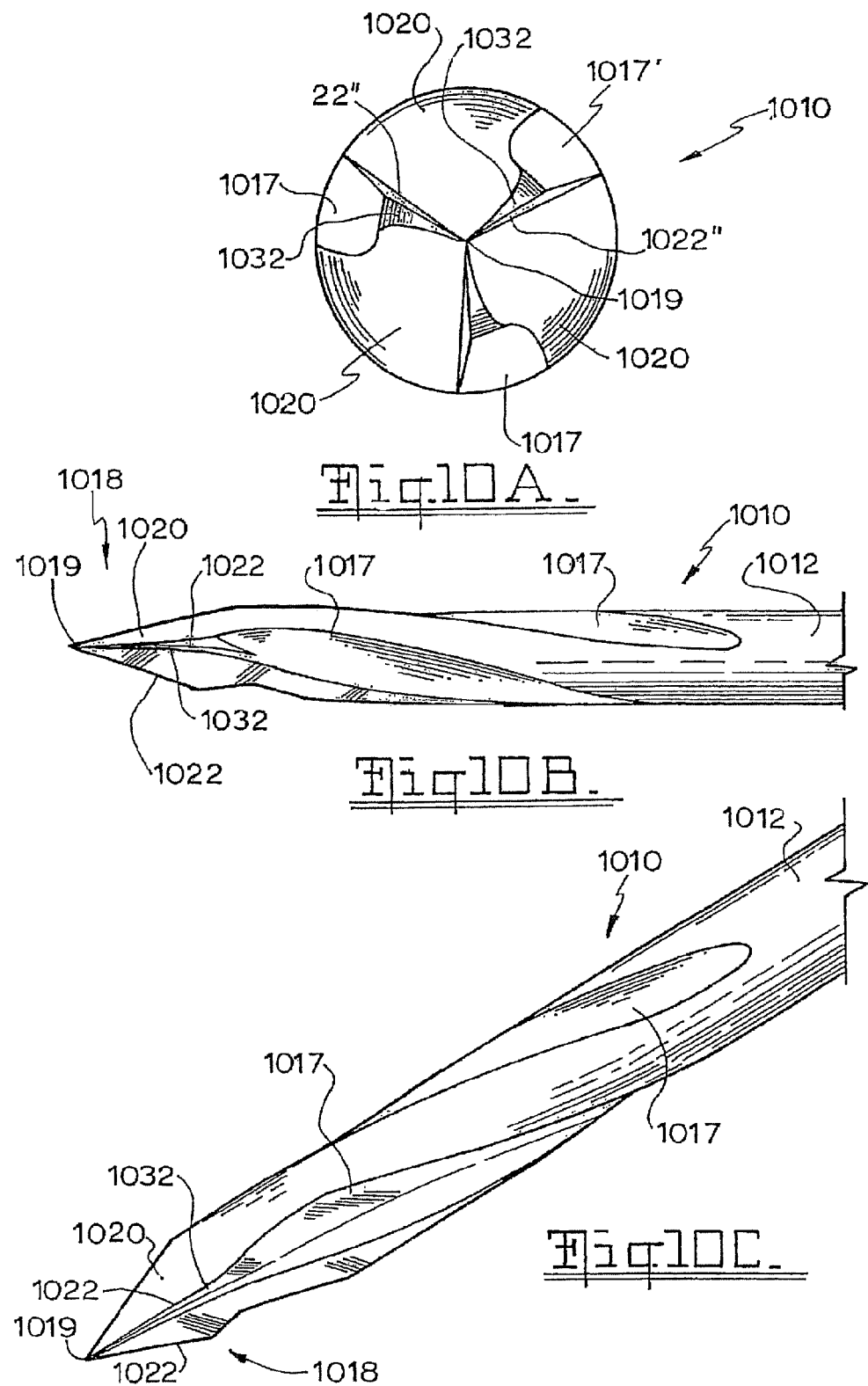
FIGS. 10A to 10C respectively show an enlarged end, and side and perspective views of a eighth drill bit in accordance with the preferred embodiment of the present invention.

Referring now to FIGS. 10A to 10C, where like reference numerals are used to denote similar or like parts, a further modified drill bit is shown. In this embodiment, the faces 1020 are typically flat (although may be slightly concave) in a similar manner to FIG. 3. Also, in this embodiment no continuous curve region at the intersection of flute 1017 and face 1020 is depicted, although such a region may be provided as appropriate.

Unique to this embodiment is the provision of a V-shaped groove 1032 running along the trailing edge 1022", from the drill point 1019 to the flute 1017. The V-shaped groove 1032 terminates in the flute 1017 and provides a further means for the channelling and directing of debris into the flute. In addition, it sharpens the leading edge 1022' of each face 1020, thus enhancing cutting. It also provides for the release of debris entrained in front of the leading edge as the drill bit rotates. The V-shaped groove 1032 can be symmetric or asymmetric as described above, with the advantages as described above.

Furthermore, in this embodiment at drill point 1019, in effect six cutting edges are provided to further enhance insertion of the drill bit through the periosteum and to promulgate rapid cutting of the drill bit into bone etc.

The operation of the drill bit of FIG. 10 is otherwise as described for the previous drill bits.

Typically the flutes, faces and grooves are machined onto the shaft 1012, and typically the shaft 1012 is formed from surgical stainless steel.

The shaft is typically cylindrical and circular in cross-section, although other cross-sectional shapes (eg. hexagonal or octagonal) may be employed.

Those skilled in the art will appreciate that the invention described herein is susceptible to variations and modifications other than those specifically described. It should be understood that the invention includes all such variations and modifications which fall within the spirit and scope of the invention.

The invention claimed is:

1. A drill bit for drilling into a surface of a material comprising:
   a shaft having a drill end, said drill end having:
   (1) a drilling end point;
   (2) a distal portion having three faces meeting at a common point defining said drill end point located on the longitudinal axis of said shaft, said three faces arranged in a pyramidal shape, said three faces defining three cutting edges; and
   (3) a proximal portion extending away from said distal portion, said proximal portion including a continuing portion of at least one face of said three faces;
   said shaft further including:
   (a) at least one flute surface defined in said shaft for directing away debris produced during drilling, said flute surface intersecting with said continuing portion of said one face of said three faces to form a first portion of a trailing edge of said one face; and
   (b) a V-shaped groove surface disposed between said drilling end point and said flute surface, said V-shaped groove surface intersecting with said continuing portion of said one face to form a second portion of the trailing edge of said one face, said V-shaped groove surface intersecting said flute surface and arranged to direct debris into said flute surface, said second portion of said trailing edge defining a piercing edge, said piercing edge enhancing insertion of said drilling end point along said longitudinal axis and into the surface of the material being drilled.

2. A drill bit according to claim 1 wherein said three faces are all substantially flat.

3. A drill bit according to claim 1 wherein said proximal portion includes a continuing portion of another face of said three faces, and wherein said continuing portion of said another face has a continuing portion of a said cutting edge.

4. A drill bit according to claim 3 wherein said flute surface intersects said continuing portion of said one face.

5. A drill bit according to claim 4 wherein said V-shaped groove surface is disposed between said continuing portion of said one face and said another face, and extends along said continuing portion of said cutting edge of said another face affecting the sharpness of said cutting edge of said another face.

6. A drill bit according to claim 1 wherein each of said faces is evenly offset with respect to the other two faces.

7. A drill bit according to claim 6 and including two additional flute surfaces.

8. A drill bit according to claim 7 wherein each of said additional flute surfaces intersects a continuing portion of a said face.

9. A drill bit according to claim 1 wherein said V-shaped groove surface terminates in said flute surface.

10. A drill bit according to claim 1 wherein said shaft is cylindrical.

11. A drill bit according to claim 1 wherein said drill bit is formed from stainless steel.

12. A drill bit according to claim 1 wherein said flute surface intersects said V-shaped groove surface.

13. A drill bit comprising:
a shaft having a drill end, said drill end having:
(1) a drilling end point;
(2) a distal portion having a plurality of faces extending from said drilling end point, each face of the plurality of faces defining a respective cutting edge, said plurality of faces arranged in a pyramidal structure; and
(3) a proximal portion extending away from said distal portion, said proximal portion including a continuing portion of at least one face of said plurality of faces;
said shaft further including:
a flute surface defined in said shaft for directing away debris produced during drilling, said flute surface intersecting with said continuing portion of said at least one face to form a first portion of a trailing edge of said at least one face and forming a terminal end; and
a second, grooved surface located at the terminal end of said flute surface and disposed between said drilling end point and said terminal end, said second, grooved surface intersecting with said continuing portion of said at least one face to form a second portion of the trailing edge of said at least one face, said second, grooved surface intersecting said flute surface and arranged to direct debris into said flute, said second portion of said trailing edge defining a piercing edge supplementing the respective cutting edges formed by the plurality of faces, said piercing edge enhancing insertion of said drilling end point along said longitudinal axis and into a surface of a material being drilled.

14. A drill bit according to claim 13 wherein said second, grooved surface is disposed between continuing portions of at least two faces of said plurality of faces to thereby affect the sharpness of a respective cutting edge formed by at least one of the two faces.

15. A drill bit according to claim 13 wherein said second, grooved surface terminates in said flute surface.

16. A drill bit according to claim 13 wherein said shaft is cylindrical.

17. A drill bit according to claim 13 wherein said drill bit is formed from stainless steel.

18. A drill bit according to claim 13 wherein said second, grooved surface is V-shaped.

19. A drill bit according to claim 13 wherein said drill bit is formed from stainless steel.

\* \* \* \* \*